(12) United States Patent
Casciari et al.

(10) Patent No.: US 6,448,287 B1
(45) Date of Patent: *Sep. 10, 2002

(54) TREATMENT OF CANCER USING LIPOIC ACID IN COMBINATION WITH ASCORBIC ACID

(75) Inventors: Joseph J. Casciari, Newton; Neil H. Riordan, Wichita, both of KS (US)

(73) Assignee: The Center for the Improvement of Human Functioning, INTL., Inc., Wichita, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,498

(22) Filed: Jul. 23, 1999

Related U.S. Application Data

(62) Division of application No. 09/249,872, filed on Feb. 16, 1999.

(51) Int. Cl.⁷ ........................ A61K 31/385; A61K 31/34
(52) U.S. Cl. ........................................ 514/440; 514/474
(58) Field of Search .................................. 514/440, 474

(56) References Cited

U.S. PATENT DOCUMENTS 5,569,670 A    10/1996   Weischer et al. ............ 514/440

FOREIGN PATENT DOCUMENTS

| EP | 0 572 922 A1 | 8/1993 |
| WO | WO 95/13061 | 5/1995 |

OTHER PUBLICATIONS

Golotyuk, Eksp. Onkol., 9(4), pp. 51–53 Abstract Only, 1987.*

* cited by examiner

*Primary Examiner*—Jerome D. Goldberg
(74) *Attorney, Agent, or Firm*—Knobbe, Martens, Olson & Bear, LLP

(57) ABSTRACT

Lipoic acid and/or its water soluble salt is used to treat cancer, alone or in combination with ascorbic acid (vitamin C). Alone or in combination, it was shown to be effective on in vitro tumors and mouse tumors. The agents can be administered safely, and have been used effectively in case studies.

14 Claims, No Drawings

TREATMENT OF CANCER USING LIPOIC ACID IN COMBINATION WITH ASCORBIC ACID

This is a Divisional of U.S. application Ser. No. 09/249,872, filed Feb. 16, 1999.

FIELD OF THE INVENTION

This invention relates generally to methods of cancer therapy and particularly the use lipoic acid as a therapeutic agent administered in combination with ascorbic acid. Ascorbate has been shown to be selectively toxic toward tumor cells, but at doses that are too high to be achieved clinically. Both lipoic acid and its water-soluble sodium salt enhance the efficacy of sodium ascorbate against three-dimensional in vitro tumors and in mouse tumors. These agents can be administered safely to patients, and in preliminary trials have been shown to stabilize or resolve disease.

BACKGROUND OF THE INVENTION

The most common methods currently in use for the treatment of cancer include surgery, radiation therapy, and chemotherapy. While these therapies are successful for some forms of the disease, they are far from universally successful in curing cancer. Moreover, traditional therapeutic regimens often cause adverse side effects such as nausea, vomiting, cardiac toxicity, bone marrow suppression, and secondary cancer. Vitamin C (ascorbic acid, ascorbate) has been proposed as an alternative to chemotherapy or as an adjuvant to lessen side effects associated with it. (For the purposes of this application, a reference to ascorbic acid includes the anionic component, ascorbate whether as an acid or one of the pharmaceutically acceptable salt thereof, most notably including sodium ascorbate and calcium ascorbate, any of which are included in a reference to "ascorbic acid" or "ascorbate"). Ascorbic acid has been thought by some to improve immune response and to prevent tumor spreading by strengthening extracellular matrix, but these theories have not as yet been conclusively proven. Clinical trials with ascorbate at doses on the order of 10 g/day were successful in some cases, but not in others. At very high doses, ascorbic acid is preferentially toxic to tumor cells. This preferential toxicity is understood to relate to the ascorbate mediated production of hydrogen peroxide, which is more toxic to tumor cells due to the lower levels of catalase typically present in tumor cells as compared to normal cells. High dose intravenous ascorbate has thus been suggested for the treatment of cancer, as described in U.S. Pat. No. 5,639,787.

Critical to the use of high dose intravenous ascorbate as an anti-cancer agent is the ability to clinically achieve plasma ascorbate levels sufficient to kill tumor cells. Previous measurements of ascorbate plasma levels following intravenous infusion demonstrate concentrations greater than those needed to kill tumor cells grown in monolayer cultures in vitro. However, much higher levels of ascorbate are required to kill tumor cells grown as three-dimensional in vitro tumors. Using the hollow fiber "solid" tumor model, it has been observed that ascorbate concentrations in excess of 500 mg/dL may be required to effectively treat tumors. Currently, the maximum plasma ascorbic acid concentration generally achievable in humans by intravenous infusion is roughly 500 mg/dL, a peak level that drops off sharply over a relatively short period of time. Although ascorbate is relatively innocuous to human patients, the need for higher plasma concentrations demonstrates a need either to safely raise effective plasma levels of ascorbate or to increase the cytotoxic effectiveness of ascorbate toward cancer cells to decrease the required dosage.

SUMMARY OF THE INVENTION

One object of the invention is to provide a method for treating cancer by administering lipoic acid and/or a water soluble salt of lipoic acid. Preferably the lipoic acid is administered at 100–1000 mg/day. More preferably at 300–600 mg/day.

A further object of the invention is to provide a method for treating cancer wherein the lipoic acid or combined therapy is used in combination with another therapy. Preferably the lipoic acid is used in combination with ascorbic acid (vitamin C). Preferably the ascorbic acid is administered intravenously at 15–700 g/week, more preferably 50–200 g/week. The preferred ratio of ascorbic acid to lipoic acid is from about 1:1 to about 3500:1, more preferably from about 10:1 to about 100:1.

A further object of the invention is to provide a pharmaceutical composition for treating cancer in a human or other animal comprising lipoic acid and ascorbic acid in an effective dose. The preferred ratio of ascorbic acid to lipoic acid is from about 1:1 to about 3500:1, more preferably from about 10:1 to about 100:1. Preferably the dose of ascorbate is 2–250 g per infusion per day. Preferably the concentration of lipoic acid is 100–1000 mg.

DETAILED DESCRIPTION OF THE INVENTION

The method of the present invention comprises the treatment of cancer by administering ascorbic acid in combination with lipoic acid in sufficient amounts to achieve a level of concentration in the patient's plasma that is cytotoxic to the cancer cells as demonstrated experimentally using in vitro culture models that mimic the in vivo solid tumor. The basis of the present invention is the discovery, through experimentation, that the concentration of ascorbate required to induce cytotoxicity in an in vitro solid tumor model is significantly reduced when the ascorbate is administered in combination with lipoic acid. Specifically, a ten to one ratio of ascorbate to lipoic acid was found to reduce the ascorbate concentration required to kill fifty percent of the tumor cells treated by roughly a factor of five over that necessary to achieve the same cell killing with ascorbate alone, i.e. a synergistic effect is achieved. This was a surprising result, since lipoic acid is a free radical scavenger that has been shown to inhibit ascorbate mediated hydrogen peroxide generation by erythrocytes. The importance of using lipoic acid in combination with ascorbate is that the level of ascorbate required for effective tumor toxicity is reduced to a level that has been successfully replicated in vivo, i.e. in the plasma of patients to whom the combination is administered through intravenous infusion.

Target levels of ascorbic acid and lipoic acid can be set according to the type of cancer afflicting the patient using in vitro studies of cytotoxicity in similar cell lines. More accurate target levels can be achieved by in vitro experimentation of malignant cells taken from the patient if such are available. This invention is not specific to a given ascorbate dose or schedule of intravenous administration. The use of one to eight hour infusions or continuous infusions with the aid of infusion pumps may be indicated. Nor is this invention specific to the vehicle of lipoic acid administration.

Further features and advantages of the present invention will become apparent to those of skill in the art in view of the detailed description of the preferred embodiments which follows when considered together with the attached drawings and claims.

DL-α-Lipoic Acid (DL-6,8-Thioctic Acid) is a lipophilic antioxidant that can be readily obtained commercially in clinical or research reagent grade. While the lipophilic form is favorable for in vivo use, some in vitro experiments were carried out using a water soluble salt produced from lipoic acid by mixing the acid with sodium bicarbonate in aqueous solution and then drying by lyophilization. For the purposes of this application, a reference to lipoic acid includes both the lipophilic acid and the water soluble salts.

Although other material and method similar or equivalent to those described herein can be used in the practice or testing of the present invention, the preferred methods and materials are now described. Example 1 describes toxicity studies that were done on cell monolayers to determine the feasibility of using the combination of ascorbic acid and lipoic acid to treat cancer.

EXAMPLE 1

Toxicity Tests in Cell Monolayers

The toxicity of ascorbic acid and lipoic acid (sodium salt) was tested in immortalized cell monolayers of both tumor and normal tissue origin. In solid tumors, proliferating cells are sometimes more sensitive to treatment than quiescent, non-proliferating cells. To investigate this in cell monolayers, we used sparse plating densities (6K/well in a 96 well plate) to allow cell proliferation and confluent densities (24K/well in a 96 well plate) to simulate quiescent cells. Cells were plated in 96 well plates at sparse or confluent densities and then incubated four days in growth medium supplemented with various doses of antioxidants. After incubation, cell numbers were determined by standard calorimetric techniques. Data were analyzed by scaling the cell number at any given antioxidant dose to that of the control and fitting the dose-response data to a sigmoid curve. Values of $LC_{50}$, the dose required to reduce cell number by fifty percent relative to untreated controls, were computed from the sigmoid data fit. Results are given in the accompanying table.

| Human Cell Types and Densities Used | | | $LC_{50}$ (mg/dL) | |
|---|---|---|---|---|
| Line | Origin | Density | Ascorbate | Lipoic Acid |
| ECV-304 | Endothelial | Sparse | 149 ± 16 | 127 ± 15 |
|  |  | Confluent | no data | no data |
| SW620 | Colon Adenocarcinoma | Sparse | 30 ± 4 | 34 ± 2 |
|  |  | Confluent | 39 ± 14 | 24 ± 2 |
| SK-MEL | Melanoma | Sparse | 15 ± 2 | 70 ± 20 |
|  |  | Confluent | 78 ± 16 | 22 ± 2 |
| Mia PaCa | Pancreatic Carcinoma | Sparse | 53 ± 6 | 80 ± 21 |
|  |  | Confluent | 308 ± 33 | 109 ± 45 |
| MCF-7 | Breast Carcinoma | Sparse | 12 ± 1 | 125 ± 31 |
|  |  | Confluent | 23 ± 3 | 60 ± 245 |

These data indicate that lipoic acid is toxic to cells at high doses; moreover, the $LC_{50}$ values for the four tumor cell lines studied (SW620, SK-MEL, Mia PaCa, and MCF-7) tended to be lower than those for the cell line derived from normal tissue (ECV-304), suggesting a greater toxicity toward tumor cells than normal cells. This was a surprising result, since there are no reports of hydrogen peroxide generation by lipoic acid; in fact, lipoic acid has been shown to inhibit ascorbate mediated hydrogen peroxide generation by erythrocytes. There seems to be little dependence of lipoic acid $LC_{50}$ on cell density, suggesting that its toxic effect is not dependent upon cell proliferation. In contrast, the data for ascorbate suggest that confluent cells were more resistant.

To determine whether the combination would work on solid tumors, in vitro tests were performed in Example 2.

EXAMPLE 2

Combination Therapy Tests in Hollow Fiber Solid in vitro Tumors

Experiments combining ascorbate and lipoic acid were carried out using the SW620 hollow fiber solid tumor model. In this in vitro tumor model, SW620 cells grow in three dimensions, forming a cylindrical tumor mass roughly 500 μm in diameter that is similar in terms of microenvironment and proliferative heterogeneity to a micro-region of a solid in vivo tumor. As with solid tumors, drugs must penetrate the inner regions of hollow fiber tumors by diffusion. This model thus provides a more formidable test for drug efficacy than cell monolayers.

SW620 hollow fiber solid tumors were grown as previously described. Briefly, PVDF hollow fibers (500 KD molecular mass cutoff, 500 mm inside diameter with a roughly 100 mm wall thickness, Spectrum Medical Co.) were prepared for cell culture use by soaking them for one week in methanol and then storing them in cell culture medium (RPMI medium supplemented with antibiotics, glutamine, and 10% fetal calf serum). SW620 colon carcinoma cells were prepared in cell culture medium at a concentration of $10^7$ cells/ml and injected into the hollow fibers. The fibers were then heat sealed at roughly 2 cm intervals to trap the cells inside them. SW620 hollow fibers were then cultured in Petri dishes for three days. After three days, the hollow fibers are transferred to stirred medium either by moving them to spinner flasks containing 50 ml cell culture medium stirred at 150 rpm by a magnetic stirrer or by transferring them to six-well plates placed on an orbital shaker at 150 rpm. Cell culture medium was replenished on days three and six. On day eight or nine, SW620 hollow fiber tumors were transferred to twenty-four-well plates containing cell culture medium supplemented with various doses of ascorbate and lipoic acid or lipoic acid sodium. After one or two days incubation on an orbital shaker, the hollow fiber tumors were rinsed and the cells were extruded out of the fibers with trypsin. The cylindrical tumor cell mass was exposed to trypsin while pipetting up and down to form a single cell suspension. Cell culture medium was then added to stop trypsin action. Surviving fractions were determined as previously described. Briefly, cells were transferred to ninety-six-well plates at a concentration of 5000 cells per well and incubated for six days. The surviving cell population was then measured using the SRB colorimetric assay. Surviving fraction was expressed as the ratio of the SRB staining at a given dose to that for cells from untreated hollow fiber tumors.

The effect of lipoic acid on SW620 hollow fibers was analyzed using dose-response curves for SW620 colon carcinoma tumor cells grown for nine days as hollow fiber tumors and treated for 48 hours with sodium ascorbate alone or in combination with lipoic acid. Lipoic acid concentrations of 5 mg/dl or 20 mg/dl were tested. The surviving fractions without ascorbate (denoted $SF_O$) were analyzed along with the doses of ascorbate required to reduce the surviving fraction to half the $SF_O$ value, denoted $LC_{50}$.

Standard deviations for $SF_O$ and $LC_{50}$ values were analyzed by the curve-fitting program KalediaGraph (Synergy Software). In this experiment the lipoic acid concentration was kept constant while the ascorbate dose was varied. It was clear from these data that lipoic acid itself, at the two concentrations tested, exhibited a toxic effect against tumor cells grown in three dimensions; moreover, lipoic acid amplified the toxic effects of ascorbate, causing reductions in surviving fraction at much lower doses than for ascorbate alone. The $LC_{50}$ value for ascorbate in the presence of 20 mg/dL lipoic acid was roughly half that in the absence of ascorbate, and the difference was statistically significant. This effect on ascorbate efficacy was not expected a priori. The ability of lipoic acid to scavenge free radicals that would otherwise be converted by ascorbate to hydrogen peroxide might suggest a protective effect rather than a toxic one. Lipoic acid, like other lipophilic antioxidants such as vitamin E, may recycle ascorbate from the reduced dehydroascorbate form. However, the effect of this recycling is uncertain: while recycled ascorbate may increase cytotoxicity due to increased hydrogen peroxide generation, any cytotoxic effects generating from the actions of ascorbate oxidation products will be reduced. Thus, the mechanism of lipoic acid's enhancement of ascorbate toxicity is unknown, though it may aid in killing quiescent cells that are resistant to ascorbate, as suggested by the cell monolayer data above.

Additional tests were carried out by varying the lipoic acid concentration with the ascorbate concentration while using a 100:1 ratio of ascorbate to lipoic acid (to yield a lipoic concentration from 5 to 10 mg/dL at the $LC_{50}$). The effect of lipoic acid in series of experiments was to again decrease the ascorbate $LC_{50}$ against SW620 hollow fiber tumors by roughly a factor of two. Since in vitro experiments with lipoic acid were limited by its hydrophobic properties, we used the hydrophilic sodium salt to lipoic acid to provide higher ascorbate to lipoic acid ratios. Specifically, a 10:1 ratio of ascorbate to the sodium salt of lipoic acid was tested against SW620 hollow fiber tumor cells. Dose response curves for SW620 colon carcinoma tumor cells grown for 9 days as hollow fiber tumors and treated for 48 hours with sodium ascorbate alone or in combination with the sodium salt of lipoic acid were prepared. In the combination treatment, the lipoic acid to ascorbate ratio was 1:10. Data from three replicate experiments were pooled. The doses of ascorbate required to reduce the surviving fraction to half the control value were denoted as $LC_{50}$. Standard deviations on $LC_{50}$ values were estimated by the curve-fitting program kaleidaGraph (Synergy Software). The results, suggest that lipoic acid sodium at this ratio can reduce the ascorbate $LC_{50}$ by roughly a factor of five, from 490 mg/dL in the absence of lipoic acid to 90 mg/dL in the presence of lipoic acid. The importance of this result is indicated by comparing the concentrations of ascorbate required for cytotoxicity in hollow fiber tumor to the doses that can be obtained in blood plasma during intravenous infusion. A plasma ascorbate concentration of 490 mg/dL is much more difficult to achieve and sustain than a value of 90 mg/dL.

To determine the feasibility of in vivo administration of the combination therapy, in Example 3 serum levels were determined after intravenous administration.

EXAMPLE 3

Studies of Ascorbate Pharmacokinetics: Implications for the Present Invention

Pharmacokinetic measurements and compartmental analysis were used to determine the potential relevance of lipoic acid and ascorbate combination therapy in the clinic. A seventy-five year old Caucasian male with diagnosed metastatic prostate cancer was infused intravenously with 65 grams sodium ascorbate in sterile water over an eighty minute period. Blood samples were taken at regular intervals over a twenty-four hour period, frozen, and then analyzed for ascorbate content using a colorimetric assay. The ascorbate plasma concentration was analyzed in a prostate cancer patient given a 60 gram intravenous infusion of sodium ascorbate over an 80 minute period. Plasma ascorbate levels measured over a 24 hour period were fit to a two compartment, four parameter pharmacokinetic model of ascorbate uptake and clearance from plasma and tissue The following parameter values were obtained: $K_X$=0.124 min$^{-1}$, $K_1$=0.124 min$^{-1}$, $K_2$=0.038 min$^{-1}$. The plasma volume $V_p$, was fixed at 30 dl. A peak plasma value of 460 mg/dL was obtained, but it quickly diminished with time. Since levels might be sustained longer with continuous infusions, the two-compartment model was used, and hypothetical plasma ascorbate curves were computed for the case of continuous twenty-four hour infusions of various ascorbate doses. Predicted plasma ascorbate levels from a two compartment, four parameter pharmacokinetic model of ascorbate transport and clearance in blood. Plasma vs. time curves are given for five different infusion doses: 25, 50, 75, 100, and 125 grams per day. The infusion rate, G(t), is set to various values as shown in the figure. Infusion is modeled as continuous. Parameter values for the compartmental model are as follows: $K_X$=0.124 min$^{-1}$, $K_1$=0.124 min$^{-1}$, $K_2$=0.038 min$^{-1}$. The plasma volume $V_p$, was fixed at 30 dl. A phase one clinical trial is currently under way to assess the safety of continuous ascorbate infusions, and is currently near completion. Doses up to 50 g/day were tested and found safe. From the modeling results in EXAMPLE 3, this dose is expected to produce plasma concentrations of roughly 52 mg/dL after twenty-four hours. Based on the data in EXAMPLE 2, SW620 hollow fiber tumor cells exposed to 52 mg/dL ascorbate for forty-eight hours would have a surviving fraction of greater than ninety percent; in contrast, the same tumor cells exposed to the same ascorbate dose combined with lipoic acid would have a surviving fraction of only sixty percent.

Thus, dose-response data with hollow fiber in vitro tumors, combined with pharmacokinetic data and modeling, suggest that ascorbate is toxic at clinically achievable doses when lipoic acid is used in combination with it. Therefore, tests were performed in an in vivo cancer model.

EXAMPLE 4

Toxicity Tests in a Murine Tumor Model

Lipoic acid alone or in combination with ascorbate (a 10:1 ascorbate to lipoic acid ratio) was tested against mouse tumors at the Beijing institute. C57 mice were divided into groups of twenty and inoculated by B16 melanoma cells subcutaneously. After forty-eight hours, treatments were administered once every other day for a five week period by subcutaneous injection near the tumor site. Tumor size was measured on days ten, seventeen, and twenty-four of treatment. The tumors in mice treated with lipoic alone or in combination with ascorbate were significantly smaller than those in the control group. Data at day twenty-four are given in the accompanying table:

| Treatment Group | Relative Tumor Size | Animal Survival |
| --- | --- | --- |
| Control | 100% | 14/20 (70%) |
| Lipoic Acid Alone | 60% (p < 0.01) | 18/20 (90%) |
| Lipoic Acid and Ascorbate | 51% (p < 0.01) | 13/20 (65%) |

Lipoic acid was toxic to mouse tumors with or without ascorbate, although animal survival rates were better for the combination. While the results for lipoic acid alone are surprising, the experiment overall confirms the utility of using lipoic acid as an anti-cancer agent in combination with ascorbate. Therefore, in the following case studies, combination therapy was initiated.

EXAMPLE 5

Case studies using the combination therapy

Case Study #1:

A sixty-five year old Caucasian female began treatment at our clinic on December $1^{st}$, 1998. In the previous year she was diagnosed by her oncologist as having low-grade small-cell malignant lymphoma with the involvement of the bone marrow. The circulating platelet count is a good indicator of metastatic burden in the bone marrow, as the expected course for this disease is for an unremitting decline in circulating platelet levels. Indeed, the patient indicated in her correspondences with our clinic that her platelet counts had fallen from 239,000 to 160,000 in the six months immediately prior to the commencement of lipoic acid therapy. She was placed on a regimen of 300 mg Lipoic Acid daily along with other nutritional supplements to accommodate her nutritional deficiencies. Two months later, She was started on intravenous vitamin C therapy, at 50 grams twice per week. Six months after her first visit, her ascorbate dose was increased to 75 grams twice per week. The patient's platelet levels remained relatively stable during the course of treatment: her counts never went below 100,000 as normally expected with this type of cancer. Six months after initiating lipoic acid treatments, her platelet count was stable at 190,000.

Case Study #2:

A 70-year-old Caucasian male was diagnosed with pancreatic cancer on December $3^{rd}$, 1996. He opted to undergo traditional chemotherapy in January, 1997. One tumor marker for pancreatic cancer is a carbohydrate antigen known as CA-19-9. The patient's antigen level decreased initially after the first chemotherapy treatment; however, by October, 1997, the his CA-19-9 level had increased to a value of 7,400 units/mL serum. At that time he was placed on a regimen of 15 grams intravenous vitamin C, given two times weekly and 300 mg oral lipoic acid, taken two times per day, as well as other nutrient supplements that the patient was deficient in. One month later his dose of Vitamin C increased to 25 grams two times per week. Within two months the patient's antigen level had dropped to 3,200 units/mL serum. At that time his dosage of Vitamin C was increased incrementally 30 grams, 50 grams, and finally 75 grams. In January, 1998, the patient opted to stop chemotherapy while continuing lipoic acid and ascorbate treatments. The levels of CA-19-9 however continued to fall. In March, 1998, the patient's CA-19-9 was 700 units/ml serum. The patients CA-19-9 levels during the time course of treatment with ascorbate and lipoic acid decreased. The levels of CA-19-9, a pancreatic cancer marker, expressed as units per mL of serum, were analyzed with time. Lipoic acid was given orally at a dose of 300 mg administered twice daily. Ascorbate was give intravenously at an initial dose of 15 grams per week. This dose was incrementally increased to 25 grams twice per week, one month after the onset of therapy, and thereafter was incrementally increased to 30, 50, and finally, 75 grams twice per week. The patient discontinued ascorbate and lipoic acid therapy in March, 1998, after six months of treatment. He died four months later.

Case Study #3:

A 53-year-old Caucasian male was diagnosed with colorectal cancer with liver metastases, and underwent surgery to remove the largest of the liver metastases. The patient was started on low dose 5-fluorouracil chemotherapy, intravenous vitamin C, and oral lipoic acid. He was also given various nutritional supplements to combat diagnosed deficiencies. The vitamin C dose was gradually increased to 100 grams, administered twice weekly by intravenous infusion. He continued therapy until March, 1998, when he was declared to be cancer-free. On his last follow-up in December, 1998, the patient was still cancer-free.

What is claimed is:

1. A method for the treatment of cancer in a mammal having cancer consisting essentially of the steps of:
   administering a synergistically effective concentration of lipoic acid or its salt in combination with ascorbic acid (Vitamin C) or its salt, wherein said cancer is sensitive to said combination, and wherein the combination is in a ratio of lipoic acid to ascorbic acid of about 1:10 to about 1:3500, and wherein the action of the lipoic acid potentiates the action of the ascorbic acid.

2. The method of claim 1, wherein said effective amount of ascorbic acid is 15 g/week to 700 g/week.

3. The method of claim 2, wherein said effective amount of ascorbic acid is 15 g/week to 200 g/week.

4. The method of claim 3, wherein said effective amount of ascorbic acid is 50 g/week to 500 g/week.

5. The method of claim 4, wherein the ratio by weight of lipoic acid to ascorbic acid is from about 1:100 to about 1:2500.

6. The method of claim 1, wherein said mammal is a human.

7. The method of claim 1, wherein the ratio of lipoic acid to ascorbic acid is 1:50–1:3500.

8. The method of claim 1, wherein the ratio of lipoic acid to ascorbic acid is 1:100–1:3500.

9. A pharmaceutical composition for treating cancer in a mammal having cancer, said composition comprising: a synergistically effective concentration of ascorbic acid (vitamin C) or its salt in combination with lipoic acid or its salt in a ratio of lipoic acid to ascorbic acid of 1:10 to about 1:3500; and a pharmaceutically acceptable vehicle, wherein said cancer is sensitive to said pharmaceutical composition, and wherein the action of the lipoic acid potentiates the action of the ascorbic acid.

10. The pharmaceutical composition of claim 9, wherein the ratio by weight of lipoic acid to ascorbic acid is from about 1:2500 to about 1:3500.

11. The pharmaceutical composition of claim 9, wherein the amount of ascorbic acid is 2–250 g.

12. The pharmaceutical composition of claim 9, wherein the amount of ascorbic acid is 100–25,000 mg.

13. The composition of claim 9, wherein the ratio of lipoic acid to ascorbic acid is 1:50–1:3500.

14. The composition of claim 9, wherein the ratio of lipoic acid to ascorbic acid is 1:100–1:3500.

* * * * *